United States Patent [19]

Kubo

[11] 3,985,615

[45] Oct. 12, 1976

[54] PROCESS FOR PREPARING LIVE VARICELLA VACCINES
[75] Inventor: Takashi Kubo, Kannonji, Japan
[73] Assignee: Research Foundation for Microbial Diseases of Osaka University, Japan
[22] Filed: Mar. 12, 1975
[21] Appl. No.: 557,724

[30] Foreign Application Priority Data
Mar. 12, 1974 Japan.............................. 49-29318

[52] U.S. Cl.................................... 195/1.3; 424/89
[51] Int. Cl.² ...................... C12K 5/00; C12K 7/00; A61K 39/12
[58] Field of Search........................ 195/1.3; 424/89

[56] References Cited
OTHER PUBLICATIONS
Andrewes et al.—Viruses of Vertebrates—2nd Edit.—1967—p. 292.

Primary Examiner—Sam Rosen
Attorney, Agent, or Firm—Burgess, Dinklage & Sprung

[57] ABSTRACT

A process for the attenuation of varicella virus comprising passaging varicella virus in a guinea pig primary embryonic tissue cell. Live avirulent varicella vaccines are also advantageously prepared by continuing the passaging until the virus is sufficiently attenuated for use as a live avirulent varicella vaccine.

4 Claims, No Drawings

PROCESS FOR PREPARING LIVE VARICELLA VACCINES

This invention relates to improvements in the biological preparation of live varicella vaccines.

More particularly, this invention is concerned with a new process for preparing a live avirulent varicella vaccine by the use of guinea pig primary embryonic tissue cells as a culture host.

Chickenpox (varicella) is one of the most common and highly communicable diseases which are attacked, primarily in childhood. A rash is generally observed over the entire body together with an attack of fever which occurs after an incubation period generally running between 14 days and 17 days. The disease results in a macular rash which may, in some cases, form pustules and, in extreme cases, leave scars. Other problems and complications may arise, for instance, in the case of undernourished children who may have necrotic dermal ulcer. Other complications such as central nervous system disturbance, myelitis and neuritis were known to occur as results from chickenpox.

Previously, various research efforts have been made in the art for adequate preventive and/or curative means, but an exact and satisfactory medicinal treatment could not yet be found or established.

As a result of my extensive studies to find out a new process for the preparation of live varicella vaccine, in particular, by the use of a novel and specific culture host, ii has been unexpectedly found that varicella vaccine can be produced in a facile and safe manner by the use of guinea pig primary embryonic tissue cells as a culture host.

It is, accordingly, a primary object of this invention to provide a process for the preparation of a live avirulent varicella vaccine wherein guinea pig primary embryonic tissue cells are utilized as a culture host.

Other objects and advantages of this invention will be apparent from the following description.

According to the present invention, there is provided a new process for the preparation of a live avirulent varicella vaccine from virulent varicella virus through a tissue culture technique characterized in that a guinea pig primary embryonic tissue cell is employed as a cultured host. As previously stated, we have found that guinea pig primary embryonic tissue cells (hereinafter frequently referred to as "GPEC") are highly suitable for the tissue culture of the virus for producing a varicella vaccine, particularly regarding (1) an excellent adaptability of the virus to the GPEC and a satisfactory growth of the virus in the GPEC for the production of the vaccine, (2) an easier availability of healthy GPEC samples with a lower cost by breeding guinea pigs under a controlled condition so that embryos may be obtained without any involved factors.

In carrying out the process of this invention, the general procedures and materials employed in a conventional tissue culture technique may be suitably applied for the present purpose. Illustratively stated, for example, embryos are taken out from healthy Hartley guinea pigs of 3 – 4 weeks pregnant stage which has been bred under an isolated condition in a vinyl isolater. The embryos are minced and suspended in a 0.25 w/v % trypsin solution. Thereafter, the cell suspension thus obtained is centrifuged and the resultant cells are suspended in Eagle's minimum essential medium containing 10 v/v % calf serum so as to provide 200,000 to 400,000 cells per ml. Aliquots of 90 to 100 ml. are poured into sterile Roux bottles and stationary culture is conducted at 36° – 37° C. for 7 days. After cell sheet is formed, the virus is inoculated.

The process of this invention is applicable to various strains of varicella virus, but the varicella virus as used hereinbelow, unless otherwise indicated, will be referred to the "Oka strain" for the purpose of illustration only. The "Oka strain" is disclosed in detail in the Abstract of Papers presented at the 20th Annual Meeting of the Japanese Society for Virology, page 2046.

In order to more fully illustrate the procedures of the present process, Examples 1 through 3 are given hereinbelow, but they should be construed to illustrate some embodiments of the present process without any intention of limiting thereto. Also, "Experiment" as given below will be served for better understanding of high effectiveness of the live avirulent varicella vaccine prepared by the present process.

Preparation of a Suspension of Varicella Virus

Varicella virus Oka strain, which had been isolated from the vesicle of chicken pox patients by the use of human embryonic lung cells, was propagated in human embryonic lung cells by successive cultivation in 11 passages. The so propagated virus was identified as varicella virus with acute and convalescent sera of varicella patients by neutralization test, complement fixation test and fluorescent antibody method. The virus thus identified was found to be able to be adapted to guinea-pig embryo culture cells.

EXAMPLE 1

Embryos were taken out from healthy Hartley guinea pigs (having no pathogenic factor) of 3–4 weeks pregnant stage which were bred under an isolated condition in a vinyl isolator. The whole embryo or skin-muscle tissues were minced with scissors and suspended in a 0.25 w/v % trypsin solution. Digestion proceeded at 37° C and the cell suspension thus obtained was centrifuged for 5 min. at 2,000 rpm, and the resultant cells were suspended in Eagle's minimum essential medium containing 10 v/v % calf serum so as to provide 200,000 to 400,000 cells per ml. Aliquots of 90 to 100 ml. were poured into sterile Roux bottles and stationary culture was conducted at 36°–37° C for 7 days. The culture medium of a monolayer of cell sheet was discarded and 5 ml. portions of a suspension of varicella virus (Oka strain) which had been obtained in the above preparation were inoculated. The virus thus inoculated was allowed to stand at 37° C for approximately 90 min. to have the virus adsorbed to the cells. Thereafter, a fresh Eagle's minimum essential medium containing 3 v/v % calf serum was poured thereto and cultivation was continued at 32°–37° C for 4 to 7 days, during which the above medium was renewed every 3 days.

After 1–3 subcultures of the virus under the above-mentioned culture conditions, microscopic examination of the culture shows roundly-shaped configuration of a guinea pig embryo cells and formation of nuclear inclusion bodies and cytopathogenic effect was confirmed. When a cytopathic effect of more than 70% of cells was observed, the GPEC was washed three times with a phosphate-buffered physiological saline solution (PBS) and a 0.2 w/v % EDTA solution was added thereto in 15 ml. portion per Roux bottle to separate out the cells, which were then collected by centrifugation at a low speed. The so collected cells were suspended into 10 ml. portion of "Tissue Culture Medium 199" per Roux bottle. The cell suspension thus prepared was treated with ultrasonic disintegration (20 kc, about 30 seconds) and centrifuged at a low speed to collect a supernatant. To the supernatant thus obtained, a stabilizer such as sucrose was added so as to be of a final concentration of 5.0 – 7.5 w/v % to produce virus suspension.

The virus thus obtained was confirmed to the varicella virus by neutralization using acute and convalescent sera from varicella patients.

EXAMPLE 2

5 ml. portions of a suspension of varicella virus (Oka Strain), which was successively cultured in GPEC in 5-passage, were inoculated onto the GPEC prepared in the same manner as in Example 1. Then, a propagated amount of the virus was measured with regard to the cultivation temperature and propagation period. The results are summarized in Table 1.

Table 1

| Temperature (°C.) | Propagation Period (days) | |
|---|---|---|
| | 4 | 7 |
| 27 | 0.8* | 1.1 |
| 30 | 1.2 | 2.2 |
| 37 | 3.3 | 3.4 |

*Data in human embryo lung cells: $\log_{10}$ (PFU/ml.)

EXAMPLE 3

The varicella virus suspension prepared by the method in Example 1 from GPEC at the 6th passage level was assayed by various tests according to the Standard for Biological Preparations set up by the Japanese Welfare Ministry in 1972 and the Official Standard set up in the United States (see The Federal Register, Vol. 34, No. 223, 1973) and then utilized as a live vaccine verified in its property and safety. The live vaccine is stored at −70° C.

EXPERIMENT

Children with no history of varicella and no antibody for varicella were injected subcutaneously with each 0.5 ml. portion of the live varicella vaccine (Oka strain) prepared from the 6th passage in GPEC as described in Example 3. The results are summarized in the following Table 2.

As is apparent from the results in Table, the vaccine prepared by the process of this invention shown safety in its clinical symptoms and high effectiveness in immunizing effect, and the minimum effective dose is 200 PFU per person. Thus it has been clearly demonstrated that varicella virus (Oka strain) passaged in GPEC is suitably attenuated and that GPEC is highly appropriate as a culture host of varicella virus for the production of a satisfactory vaccine.

The vaccine is dispensed in 0.5 ml. amount in ampoule with the virus dose of 200 to 1,000 PFU. The vaccine can be stored at −70° C in frozen state without significant loss of infectivity for 1 year. In addition, the vaccine can be lyophilized in 0.5 ml. amount in ampoule, which can be stored at 4° C. For practical use, the frozen virus is thawed and the lyophilized virus is dissolved with distilled water, and 0.5 ml. portions are injected subcutaneously into subject.

Table 2

| Inoculated amount of virus | Sex | Age | Antibody titer in blood* | | Clinical manifestation |
|---|---|---|---|---|---|
| | | | Before inoculation | 30 days after inoculation | |
| | m | 4.2 | < 4 | 64 | not observed |
| | f | 6.1 | < 4 | 64 | " |
| | m | 3.0 | < 4 | 16 | " |
| | m | 2.4 | < 4 | < 4 | " |
| | m | 3.9 | < 4 | 8 | " |
| | m | 2.5 | 4 | 16 | " |
| | f | 1.5 | 4 | 16 | " |
| | f | 1.9 | < 4 | 16 | " |
| | f | 6.1 | < 4 | 8 | " |
| | f | 8.3 | < 4 | 4 | " |
| 500 PFU** | m | 3.5 | < 4 | 4 | " |
| | m | 1.9 | < 4 | 4 | " |
| | m | 1.3 | < 4 | 8 | " |
| | m | 7.1 | < 4 | 16 | " |
| | f | 5.3 | < 4 | 16 | " |
| | m | 5.4 | < 4 | 4 | " |
| | f | 4.1 | < 4 | 8 | " |
| | m | 3.1 | < 4 | 64 | " |
| | f | 2.5 | < 4 | 32 | " |
| | f | 2.7 | < 4 | 32 | " |
| | f | 5.4 | < 4 | 4 | not observed |
| | f | 3.3 | < 4 | 64 | " |
| | m | 2.4 | < 4 | 4 | " |
| | m | 3.5 | < 4 | 8 | " |
| | m | 4.7 | < 4 | 64 | " |
| | f | 3.7 | < 4 | 8 | " |
| 200 PFU | m | 3.8 | < 4 | 16 | " |
| | m | 4.6 | < 4 | 8 | " |
| | f | 1.1 | < 4 | 4 | " |
| | f | 5.3 | < 4 | 16 | " |
| | f | 2.4 | < 4 | 16 | " |
| | m | 5.5 | < 4 | < 4 | " |

*The virus Oka strain successively cultured in human embryonic lung cells was utilized as an antigen for the measurement in a complement fixation test.
**PFU: Plaque Forming Unit (in human embryonic lung cells)

What is claimed is:

1. A process for the attenuation of varicella virus comprising passaging the varicella virus in a guinea pig primary embryonic tissue cell at a temperature of 32° – 37° C until the virus is adequately attenuated.

2. A process for the preparation of a live avirulent varicella vaccine from virulent varicella virus by passaging in a tissue culture technique, characterized in that a guinea pig primary embryonic tissue cell is employed as a culture host at a temperature of 32–37° C, passaging is continued until the virus is adequately attenuated, and the virus is thereafter separated from the culture host, such virus being suitable for administration as a vaccine.

3. A process according to claim 2 wherein the strain of said varicella virus is the Oka strain.

4. A process according to claim 2 wherein the virus is passaged about 5 or 6 times in the guinea pig primary embryonic tissue cell culture host.

* * * * *